United States Patent [19]

Nelan et al.

[11] 4,239,691
[45] Dec. 16, 1980

[54] CONVERSION OF NON-ALPHA-TOCOPHEROLS TO ALPHA-TOCOPHEROLS

[75] Inventors: Donald R. Nelan; Charles H. Foster, both of Kingsport, Tenn.

[73] Assignee: Eastman Kodak Company, Rochester, N.Y.

[21] Appl. No.: 45,555

[22] Filed: Jun. 4, 1979

[51] Int. Cl.³ .......................................... C07D 311/72
[52] U.S. Cl. .................................................. 260/345.5
[58] Field of Search ........................ 260/345.6, 345.5; 568/764

[56] References Cited

U.S. PATENT DOCUMENTS

| 2,486,540 | 11/1949 | Hickman et al. | 260/345.6 |
| 2,592,628 | 4/1952 | Weiser | 260/345.5 |
| 3,122,565 | 2/1964 | Kijima et al. | 260/345.6 |
| 3,402,182 | 9/1968 | Kijima et al. | 260/345.6 |
| 3,631,068 | 12/1971 | Nelan | 260/345.5 |
| 3,819,657 | 6/1974 | Baldwin et al. | 260/345.6 |

*Primary Examiner*—Nicky Chan
*Attorney, Agent, or Firm*—John F. Stevens; Daniel B. Reece, III

[57] ABSTRACT

A process for producing alpha-tocopherol from non-alpha-tocopherols comprising reacting the tocopherol with formaldehyde, carrying out the reaction at a temperature of at least about 175° C. in the presence of a catalytic amount of an acidic ion exchange resin and subjecting the reaction mixture to catalytic hydrogenation.

9 Claims, No Drawings

CONVERSION OF NON-ALPHA-TOCOPHEROLS TO ALPHA-TOCOPHEROLS

BACKGROUND OF THE INVENTION

1. Field of the Invention

This invention relates to a process for converting non-alpha-tocopherols to alpha-tocopherol.

2. Description of Prior Art

Various processes are known in the art for converting non-alpha-tocopherols to alpha-tocopherol, a form which has relatively high Vitamin E activity compared to the beta-, gamma- and delta- forms. For example, U.S. Pat. No. 2,592,628 (the disclosure of which is incorporated herein by reference) discloses subjecting tocopherols having at least one aromatic hydrogen atom on the nucleus to formylation to replace the aromatic hydrogen atom or atoms with formyl groups and reducing the formylated tocopherol material, whereby the formyl groups are reduced to methyl groups. Also, U.S. Pat. No. 3,819,657 discloses that non-alpha-tocopherols can be converted to the alpha form using formaldehyde in the presence of orthophosphoric acid (or an orthophosphoric acid generating material) and catalytic hydrogenation. Conversions of as high as 92% are reported in this patent.

U.S. Pat. Nos. 3,122,565 and 3,402,182 disclose use of basic anion exchange resins in the purification or separation of tocopherols.

BRIEF DESCRIPTION OF THE INVENTION

The process according to the present invention provides for the conversion of non-alpha-tocopherols (e.g., beta-, gamma-, and delta-tocopherols) to alpha-tocopherol by the use of an acidic ion exchange resin and hydrogenation catalyst at temperatures of about 175° C. or higher. Conversions which are essentially quantitative are obtained.

DETAILED DESCRIPTION OF THE INVENTION

According to the present invention, non-alpha-tocopherols are converted to alpha-tocopherol by a hydroxymethylation-hydrogenation process which is catalyzed by an insoluble acidic ion exchange resin. The predominant forms of tocopherol are represented by the structure

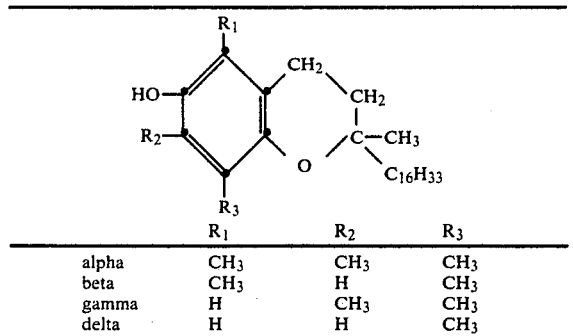

|       | R₁  | R₂  | R₃  |
|-------|-----|-----|-----|
| alpha | CH₃ | CH₃ | CH₃ |
| beta  | CH₃ | H   | CH₃ |
| gamma | H   | CH₃ | CH₃ |
| delta | H   | H   | CH₃ |

Tocopherols are contained in abundance in vegetable oils and, in most cases, several homologs are present as a mixture. In nature, non-alpha-tocopherols often coexist with alpha-tocopherol. In the process of the present invention, the existence of such alpha-tocopherol in the raw material does not interfere with the reaction. Therefore, in the process of the present invention, even if the raw material is in the state of a crude mixture obtained from a vegetable oil, the purposes of the invention will be able to be accomplished.

According to the process of the present invention, non-alpha-tocopherols which normally exist in a mixture of beta, gamma and delta tocopherol are dissolved in a suitable solvent with formaldehyde and subjected to simultaneous hydroxymethylation-hydrogenation using an insoluble cation exchange resin and hydrogenation catalyst at elevated temperature and pressure. The reaction mixture is then cooled, washed and dried. The process is found to yield essentially quantitative conversion of the non-alpha-tocopherols to alpha-tocopherol.

The tocopherol mixture is dissolved in a solvent or mixture of solvents, preferably a lower primary alcohol ($C_1$–$C_4$) such as methanol, with a source of formaldehyde. In batch reaction mixture, paraformaldehyde (a solid) may conveniently be used, but in the preferred continuous process, formaldehyde in solution such as methanol is preferred. Alternatively formaldehyde derivatives, such as dimethoxymethane or trioxane, may be used. A sufficient quantity of solvent is used to form a suitable solution. Normally, the weight ratio of tocopherol to formaldehyde will be at least 1.5:1, preferably about 2:1. No advantage is obtained in using a ratio of greater than about 2.5:1.

A catalytic amount of a suitable insoluble acidic cation exchange resin is used. Normally, in a continuous reaction, the amount of such resin is greater, by weight, than the tocopherol mixture.

Suitable acid ion exchange resins are described in Kirk-Othmer Encyclopedia of Chemical Technology, 2nd Edition, Volume 71, pages 873-875. Acid ion exchange resins are exemplified by the principal sulfonated styrene-divinylbenzene copolymer products (Amberlite IR-120, Amberlite IR-200, Dowex 50, Dowex 50W, Dowex MPC-1, Duolite C-20, Duolite C-25, Ionac C-250). A preferred acidic ion exchange resin is Nafion resin because of its stability at high temperatures.

The producers of these resins are:

| Company | Trademark |
|---------|-----------|
| Diamond Alkali Co. | Duolite |
| The Dow Chemical Co. | Dowex |
| Ionac Chemical Corp. | Ionac |
| Rohm & Haas Co. | Amberlite |
| Du Pont | Nafion |

A preferred resin prepared by polymerizing perfluoroethylene with a perfluorovinyl ether containing attached sulfonic acid groups has the following structure:

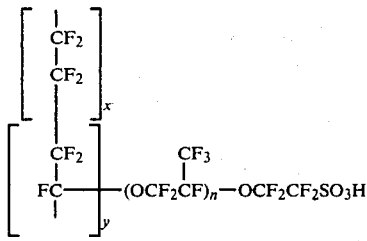

wherein n=1 or 2 and the ratio of x over y varies from about 2 to about 50. The polymer of structure V is available commercially under the tradename of Nafion resin.

Hydrogenation catalysts are well known in the art. For example, a noble metal such as palladium, preferably on charcoal, may be used.

The reaction may be carried out by charging all of the material into a suitable reaction vessel, pressurizing the vessel with hydrogen and then heating the reaction mixture. It is preferred that the reaction mixture be heated to at least about 175° C. for a sufficient length of time to complete the reaction. The temperature should not be so high as to cause decomposition of the reactants or products and is preferably held below 300° C. The reaction is normally less than about 10 hours, usually from about 2 to 6 hours. Preferred hydrogenation pressures of about 500 to 2500 psig are used. The reaction can be carried out on a continuous basis using equipment and fixed bed catalyst well known to those skilled in the art.

The following examples are submitted for a better understanding of the invention.

EXAMPLE 1

A tocopherol concentrate (22.4 g, containing 76.5 mg/g alpha, 225 mg/g gamma, and 79 mg/g delta), methanol (40 ml), paraformaldehyde (9.6 g) Dowex 50-W acidic ion exchange resin (8.4 g) and 5% palladium on charcoal (0.75 g) are combined in an autoclave. The autoclave is charged with 800 psig hydrogen and heated to 200° C. for eight hours. The reaction mixture is cooled, diluted with hexane, washed three times with water, and dried. The hexane is evaporated and the product is analyzed by gas chromatography. The conversion of non-alpha-tocopherol to alpha-tocopherol is essentially quantitative.

EXAMPLE 2

A tocopherol concentrate (same as in Example 1, 23.2 g), methanol (50 ml), paraformaldehyde (9.6 g), and Dowex 50-W acidic ion exchange resin, 5% palladium on charcoal (recovered from Example 1) are combined in an autoclave. The reaction time, temperature, and hydrogen pressure are the same as in Example 1. The product is analyzed by gas chromatography and found to have the same tocopherol composition as in Example 1. Thus, the conversion is essentially quantitative.

EXAMPLE 3

A tocopherol concentrate (20 g, containing 123 mg/g alpha, 431 mg/g gamma, and 119 mg/g delta) in methanol (40 ml), paraformaldehyde (10 g), Amberlite 200 acidic ion exchange resin (5 g) and 5% palladium on charcoal (1 g) are combined in an autoclave. The autoclave is charged with 800 psig hydrogen and heated to 200° C. for 2 hours. The product is isolated and analyzed by gas chromatography. The concentrate contains 658 mg/g alpha, 19 mg/g gamma and 5 mg/g delta. The conversion of non-alpha-tocopherols to alpha-tocopherol is essentially quantitative.

EXAMPLE 4

A tocopherol concentrate (50 g containing 76.5 mg/g alpha, 207.7 mg/g gamma, 89.2 mg/g delta), methanol (225 ml), 55% formaldehyde in methanol (44 g), Nafion 501 acidic ion exchange resin (10 g) and 5% palladium on charcoal (2.0 g) are combined in an autoclave. The autoclave is charged with 800 psig hydrogen and heated to 200° C. for 4 hrs. The isolated product analyzed by gas chromatography contains 391 mg/g alpha, 5 mg/g gamma, 9 mg/g beta, and 1 mg/g delta. The conversion of non-alpha-tocopherols to alpha-tocopherol is essentially quantitative.

EXAMPLE 5

30.0 g Tocopherol concentrate containing 76 mg/g alpha-tocopherol, 238 mg/g gamma-tocopherol, and 89 mg/g delta-tocopherol (403 mg/g-total tocopherol) dissovled in 125 ml methanol and 25 ml heptane is combined with 44 g of a methanol solution of formaldehyde (50%). The solution is fed at a constant rate to a preheated column (200° C.) packed with a mixture of equal amounts of 0.5% palladium on carbon pellets and Nafion acidic ion exchange resin pellets. The initial atmosphere of the column is 800 psi of hydrogen. The solvent from the crude product after passing through the column is evaporated and the residue is analyzed by glc. The conversion (391 mg/g alpha-tocopherol) is essentially quantitative.

Unless otherwise specified, all parts, percentages, ratios, etc., are by weight.

The invention has been described in detail with particular reference to certain preferred embodiments thereof, but it will be understood that variations and modifications can be effected within the spirit and scope of the invention.

We claim:

1. In the process for producing alpha-tocopherol from non-alpha-tocopherols having at least one hydrogen atom in the benzene nucleus comprising reacting the tocopherol with a formaldehyde source, the improvement comprising carrying out said reaction at a temperature of at least about 175° C. in the presence of a catalytic amount of an acidic ion exchange resin and subjecting the reaction mixture to catalytic hydrogenation.

2. The process of claim 1 wherein the reaction is carried out in the presence of a solvent.

3. The process of claim 2 wherein said solvent is a primary alcohol having from 1 to 4 carbon atoms.

4. The process of claim 1 wherein said formaldehyde source is formaldehyde dissolved in methanol.

5. The process of claim 1 wherein said formaldehyde source is paraformaldehyde.

6. The process of claim 1 wherein said hydrogenation reaction is carried out continously on a fixed bed catalyst.

7. The process of claim 1 wherein said tocopherol-formaldehyde reaction is carried out at a temperature of between about 175° C. and about 300° C. and wherein said hydrogenation reaction is carried out at a hydrogen pressure of between about 500 and about 2500 psig.

8. The process of claim 1 wherein said non-alpha-tocopherols comprise alpha-, beta-, gamma-, and delta-tocopherols.

9. In the process for producing alpha-tocopherol from a mixture of alpha-, beta-, gamma-, and delta-tocopherols wherein said mixture is reacted with a formaldehyde source, the improvement comprising carrying out said reaction at a temperature of between about 175° C. and about 300° C. in a continuous manner in the presence of a catalytic amount of an acidic ion exchange resin and subjecting the reaction mixture to hydrogenation over a fixed bed catalyst at a hydrogen pressure of between about 500 and about 2,500 psig.

* * * * *